United States Patent [19]

Willard, Sr.

[11] 3,984,540
[45] Oct. 5, 1976

[54] METHOD OF THERAPEUTICALLY TREATING DAMAGED AND/OR INFECTED TISSUE IN WARM BLOODED ANIMALS AND COMPOSITIONS THEREFOR

[75] Inventor: John W. Willard, Sr., Rapid City, S. Dak.

[73] Assignee: CAW Industries, Inc., Rapid City, S. Dak.

[22] Filed: Mar. 26, 1974

[21] Appl. No.: 455,022

Related U.S. Application Data

[63] Continuation-in-part of Ser. No. 317,097, Dec. 20, 1972, Pat. No. 3,893,943, which is a continuation of Ser. No. 108,198, Jan. 20, 1971, abandoned.

[52] U.S. Cl. .............................. 424/116; 424/115; 424/153; 424/154; 424/181; 424/227; 424/246; 424/271; 424/324
[51] Int. Cl.² ................. A61K 33/06; A61K 33/14; A61K 35/66
[58] Field of Search .......... 424/180, 271, 153, 155, 424/154, 181, 227, 246, 115, 116, 324

[56] References Cited
OTHER PUBLICATIONS
The Merck Veterinary Manual – 2nd edit. (1961), pp. 510 and 511.

Primary Examiner—Sam Rosen
Attorney, Agent, or Firm—L. S. Van Landingham, Jr.

[57] ABSTRACT

Tissue in warm blooded animals which is damaged and/or infected is treated by administering a therapeutically effective amount of a novel catalyst or synergist. The treatment is effective in relieving stress and/or shock. In a further variant warm blooded animals having damaged and/or infected tissue are treated with a composition containing a therapeutically effective amount of at least one antibiotic and the catalyst or synergist. Novel therapeutic compositions are provided which contain at least one antibiotic and an effective amount of the catalyst or synergist. The catalyst or synergist is prepared by steps including admixing a water soluble alkali metal silicate with an aqueous medium containing carefully controlled amounts of dissolved water soluble substances which are sources of calcium ion and magnesium ion, reacting the same to produce an aqueous colloidal suspension of the reaction product, admixing a micelle forming surfactant with the aqueous medium, and agitating the aqueous medium containing the colloidal particles and surfactant to form micelles containing the colloidal particles.

38 Claims, No Drawings

METHOD OF THERAPEUTICALLY TREATING DAMAGED AND/OR INFECTED TISSUE IN WARM BLOODED ANIMALS AND COMPOSITIONS THEREFOR

RELATED APPLICATIONS

This application is a continuation-in-part of copending application Ser. No. 317,097, filed Dec. 20, 1972 on behalf of John W. Willard, Sr. for Novel Catalyst And Process For Preparing The Same, and now U.S. Pat. No. 3,893,943 application Ser. No. 317,097, in turn, is a continuation of application Ser. No. 108,198, filed Jan. 20, 1971, now abandoned.

BACKGROUND OF THE INVENTION

This invention broadly relates to the treatment of warm blooded animals with a therapeutically effective amount of a novel catalyst or synergist. In a further variant, the invention relates to the therapeutic treatment of warm blooded animals with antibiotics in the presence of a catalyst or synergist. The invention further relates to novel therapeutic compositions which are useful in practicing the method of the invention.

A wide variety of pharmacologically active substances have been proposed heretofore for use in treating diseased and/or damaged tissue in warm blooded animals. However, the pharmacological formulations available heretofore generally have not had a combination of desirable properties including pronounced antibacterial and/or antifungal activity, an ability to promote the curing of infections and/or the rebuilding of damaged tissue, an ability to markedly reduce stress and/or shock, a nonpoisonous nature and capable of being administered as often as desired without harmful effect. Further, entirely satisfactory pharmacological formulations for the open wound healing of infected and/or damaged tissue including cuts, sores, burns, sprains, bruises, skin irritations and infections have not been available heretofore. A pharmacological formulation capable of acting as a catalyst or synergist when administered in combination with one or more antibiotics also has not been available heretofore.

The present invention provides a catalyst or synergist which has the aforementioned desirable properties when used alone in the therapeutic treatment of warm blooded animals. In addition thereto, it may also be used in the treatment of warm blooded animals with antibiotics to increase the effectiveness thereof by a synergistic action. Thus, the novel catalyst or synergist of the invention has a combination of unusual and unexpected properties which have not been possessed heretofore by pharmalogical formulations in present use.

It is an object of the present invention to provide a novel method of therapeutically treating damaged and/or infected tissue in warm blooded animals.

It is a further object to provide a novel method of relieving stress and shock in warm blooded animals.

It is a further object to provide a novel method of markedly increasing the therapeutic effectiveness of an antibiotic administered to a warm blooded animal.

It is a further object to provide a novel method of treating a warm blooded animal which employs a composition containing a therapeutically effective amount of an antibiotic and a catalyst or synergist.

It is a further object to provide novel therapeutic compositions which are useful in practicing the invention.

Still other objects and advantages of the invention will be apparent to those skilled in the art upon reference to the following detailed description and the specific examples which are for purposes of illustration only.

DETAILED DESCRIPTION OF THE INVENTION INCLUDING PREFERRED VARIANTS THEREOF

In accordance with one important variant of the present invention, warm blooded animals having damaged and/or infected tissue are therapeutically treated by administering an effective amount of a novel catalyst or synergist. In accordance with a second variant of the invention, warm blooded animals having damaged and/or infected tissue are treated with a synergistic combination containing a therapeutically effective amount of at least one antibiotic and the novel catalyst or synergist of the invention. In accordance with a third variant of the invention, synergistic compositions are provided which contain a therapeutically effective amount of at least one antibiotic and the novel catalyst or synergist of the invention. Each of these three variants will be described in detail hereinafter. Also, the novel catalyst or synergist, which will hereinafter be referred to as a catalyst for the purpose of simplifying the discussion, will be described more fully hereinafter.

In practicing the aforementioned first variant of the invention, the catalyst may be administered by topical application of a liquid suspension of the catalyst or in dry form, or by parenteral injection of a liquid suspension of the catalyst, or orally in liquid or solid form. Preferably, the catalyst is in the form of an aqueous suspension as it may be easily administered by topical application to the infected or damaged area, or by parenteral injection, or orally such as in drinking water or food. The catalyst need be administered only in catalytic amounts. For example, 0.0000–0.1% or less of the catalyst based upon body weight may be administered orally or by parenternal injection. In instances where a composition containing the catalyst is applied then it may contain, for example, about 0.000001–1% of the catalyst or less. While aqueous suspensions of the catalyst are usually preferred, other liquid pharmaceutically acceptable carriers may be used. Additionally, a dry catalyst may be administered in some instance with good results such as when it is administered orally in the form of powder, tablets or capsuls. The catalyst is harmless in reasonable amounts such as up to 1% of body weight and it may be administered as often as is desired without harmful effect. However, usually one to three applications or doses per day are adequate and additional applications are not beneficial.

The aqueous catalyst suspension is especially effective in open wound healing and in treating cuts, open sores, burns, foot rot, pink eye, splints, saddle gall, skin irritations and infections, and the like in domestic animals such as dogs, cats, cattle, sheep, horses and poultry. The presence of a catalytically effective amount of the catalyst promotes the rate of healing of damaged tissue very markedly and there is a much faster recovery. The aqueous catalyst suspension also exhibits very powerful antibacterial and antifungal properties and thus it is useful in fighting infections in general of the types commonly contacted by domestic animals. In addition thereto, the catalyst has a pronounced soothing effect and it is capable of relieving stress and/or shock. The catalyst may be used for this purpose alone in instances where controlling stress and/or shock is an important factor in the successful treatment of a warm blooded animal.

In instances where the aqueous catalyst suspension is applied topically, then often it is preferred that an ultraviolet light absorber be added. An example of one presently preferred ultraviolet light absorber is Gentian Violet. Following topical application of the catalyst suspension, the ultraviolet light absorber is thought to absorb ultraviolet light at the site of the damaged or infected tissue and thereby aid in promoting the rapid repair and healing thereof, and/or to control infections.

The catalyst is very effective in preventing, controlling or therapeutically treating infections of the digestive tract of domestic animals such as, respiratory infections in general such as pneumonia, and diseases commonly contacted by poultry. It is usually preferred that the catalyst be administered daily in drinking water and/or in feed and especially when preventing or controling infections. Parenternal injection may also be useful in some instances.

In accordance with the aforementioned second variant of the invention, one or more antibiotics may be administered to a warm blooded animal in combination with a catalytic amount of the catalyst. The specific antibiotic to be administered in a given instance, the amount, and the method of administering the same may be in accordance with prior art practice. However, usually much smaller quantities of the antibiotic are needed to produce comparable results. Often only one-third to two-thirds as much of the antibiotic as is normally required need be administered.

The catalyst may be administered along with the antibiotic or separately therefrom. The methods of administering the synergistic combination of the antibiotic and the catalyst may be as given hereinbefore for the catalyst alone. The quantity of the catalyst to be administered also may be as aforementioned, but is understood that the dosage may vary widely in view of the catalyst being harmless and the fact that only a catalytic amount of the catalyst need be present.

Surprisingly, the synergistic combination of the antibiotic and the catalyst often is useful in treating infections where the antibiotic alone or the catalyst alone is of little therapeutic value. For example, the synergistic combination of the antibiotic and catalyst is highly effective in treating foot rot in cattle and sheep whereas treatment with either component alone will not result in a permanent cure.

The synergistic combination of the antibiotic and catalyst may be used in treating all of the diseases treated heretofore with antibiotics alone. Examples of antibiotics which may be used in practicing the invention are as follows:

| amicetin | erythromycin | pactamycin |
|---|---|---|
| aureomycin | furacin | penicillin |
| aureotracin | gentamicin | polymyxin |
| bacitracin | grisonomycin | protomycin |
| bleomycin | halomicin | spiramycin |
| carbomycin | libanomycin | streptomycin |
| coumermycin | lincomycin | streptothicin |
| cephalasporins | melanomycin | telomycin |
| chalcomycin | methicillin | tetracycline |
| chlorotetracycline | mitomalcin | tetramycin |
| chromomycin | moenomycin | thioaurin |
| condicidin | novobiocin | zygomycin |
| cycloserine | neomycin | |
| endomycin | oligomycin | |

The preparation of antibiotics such as those aforementioned and/or the use thereof in the treatment of infections in warm blooded animals is disclosed in numerous publications, including the following U.S. Pat. Nos.:

| | | |
|---|---|---|
| 2,442,006 | 2,990,330 | 3,323,998 |
| 2,443,962 | 2,992,162 | 3,350,267 |
| 2,572,897 | 3,008,875 | 3,351,582 |
| 2,602,041 | 3,023,105 | 3,359,164 |
| 2,633,445 | 3,023,145 | 3,501,570 |
| 2,743,268 | 3,061,516 | 3,510,555 |
| 2,746,902 | 3,065,137 | 3,511,909 |
| 2,749,273 | 3,067,100 | 3,644,617 |
| 2,751,324 | 3,089,827 | 3,665,003 |
| 2,795,528 | 3,147,184 | 3,681,491 |
| 2,909,464 | 3,155,587 | 3,696,194 |
| 2,927,057 | 3,205,137 | 3,708,477 |
| 2,943,024 | 3,279,923 | 3,708,480 |
| 2,943,025 | 3,304,231 | 3,772,438 |
| 2,963,403 | 3,313,691 | |

The teachings of the above United States patents are incorporated herein by reference.

The present invention also provides novel therapeutic compositions containing a synergistic combination of one or more antibiotics and the catalyst. A pharmaceutically acceptable carrier may be present when desired. Such synergistic compositions may be administered to a warm blooded animal in accordance with prior art practice for the antibiotic alone and the treatment may be continued until the infection is cleared up and/or the tissue is healed.

The reasons for the unusual and unexpected therapeutic properties of the catalyst when used alone are not fully understood at the present time. However, it is thought that the catalyst promotes or synergizes beneficial reactions between the infected and/or damaged tissue and body fluids, air and/or water or components thereof in contact with the tissue, and thereby provides an environment which is beneficial in controlling infections in infected tissue and/or promoting the healing of damaged tissue. When the catalyst is used in combination with an antibiotic, it acts as a synergist and increases the effectiveness of a given dose of the antibiotic, and allows less antibiotic to be used for a given degree of effectiveness. In a number of instances, the synergistic combination is capable of providing a cure for diseases such as cancer eye for the first time.

The novel catalyst or synergist of the invention is described in greater detail hereinafter.

PREPARATION OF THE CATALYST

The catalyst used in practicing the present invention may be prepared as described below. In the presently preferred process for preparing an aqueous suspension of the catalyst, a water soluble alkali metal silicate is admixed and reacted with an aqueous solution of a water soluble dissolved substance which is a source of calcium ion and a water soluble dissolved substance which is a source of magnesium ion to produce a finely divided or colloidal suspension of the reaction product. The aqueous solution contains the dissolved substances initially in amounts to provide between about $1 \times 10^{-4}$ and $1 \times 10^{-1}$ mole per liter each of calcium ion and magnesium ion, preferably between about $1 \times 10^{-3}$ and $1 \times 10^{-2}$ mole per liter, and for still better results between $1 \times 10^{-3}$ and $6 \times 10^{-3}$ mole per liter. The dissolved substances should also be present in amounts to provide a molar ratio of calcium ion to magnesium ion between about 2.0:1.0 and 1.0:2.0, and preferably about 1.5:1.0 and 1.0:1.5. For best results, the aqueous medium should contain the dissolved substances in amounts to provide between about $2.5 \times 10^{-3}$ and $3.0 \times 10^{-3}$ mole per liter each of calcium ion and magnesium ion, and the molar ratio of calcium ion to magnesium ion should be about 1.0:1.0, e.g., $2.9 \times 10^{-3}$ mole per liter of calcium ion and $2.7 \times 10^{-3}$ mole per liter of magnesium ion. The alkali metal silicate should have an alkali metal oxide to silicon dioxide ratio between about 0.9:1.0 and less than 2.0:1.0, and preferably between about 0.9:1.0 and 1.2:1.0. The alkali metal silicate should be admixed with the aqueous medium in an amount of about 0.05–2 moles per liter, preferably about 0.1–1 mole per liter, and for still better results about 0.2–0.5 mole per liter. For best results, the alkali metal silicate should be an alkali metal meta-silicate having an alkali metal oxide to silicon dioxide ratio of about 1:1, and it should be admixed with the aqueous medium in an amount to provide about 0.2–0.3 mole per liter, e.g., about 0.25 mole per liter.

Examples of sources of calcium ion and magnesium ion for use in preparing the aqueous solution include mineral acid salts such as the halides, sulfates, bisulfates, nitrites, and nitrates of calcium and magnesium. The chlorides are usually the preferred halides, and both calcium and magnesium chloride are soluble and may be used. Magnesium sulfate and bisulfate are soluble and often are the preferred sources of magnesium ion. Calcium sulfate is only slightly soluble in water and usually is not a preferred source of calcium ion, but calcium bisulfate is somewhat more soluble. While calcium and magnesium nitrite or nitrate are soluble in water and may be used, these substances are not preferred in most instances. The sources of calcium ion and magnesium ion are dissolved in the aqueous medium in amounts to provide calcium ion and magnesium ion within the above ranges. Complete ionization is assumed when calculating the quantities to be dissolved and any desired order of addition is satisfactory. For example, the source of calcium ion may be added to the aqueous medium before, during or after the source of magnesium ion.

The alkali metal silicate to be admixed with the aqueous medium is preferably a water soluble sodium or potassium silicate having an alkali metal oxide ($M_2O$) to silicon dioxide ($SiO_2$) mole ratio between about 0.9:1.0 and less than 2.0:1.0, and preferably between about 0.9:1.0 and 1.2:1.0. The best results are usually obtained with an alkali metal mestasilicate having an alkali metal oxide to silicon dioxide ratio of about 1:1. Hydrated alkali metal silicates dissolve faster and should be used for best results when the alkali metal silicate is added in solid form. In instances where an anhydrous alkali metal silicate is used, it may be desirable to dissolve it in water and then add the solution to the aqueous medium. Sodium metasilicate is preferred and usually a hydrated sodium metasilicate such as the pentahydrate gives the best results.

Carbonate ion and/or bicarbonate ion should not be present in the aqueous medium in substantial concentrations as the calcium ion and magnesium ion are precipitated in the form of their respective carbonates. The free carbonate ion and/or bicarbonate ion concentrations in the aqueous medium should not exceed about 10 parts per million by weight based upon the combined weight of the water and the ingredients added thereto and for this reason, the alkali metal silicates should be substantially free of carbonate ion and bicarbonate ion. A small amount of precipitated calcium carbonate and/or magnesium carbonate may be present in the aqueous medium provided additional calcium ion and magnesium ion are available to meet the above defined concentrations.

Distilled water and/or deionized water are usually preferred over a natural or untreated water when preparing the aqueous medium. In instances where water is used which contains substantial initial concentrations of alkaline earth metal ions, then this should be taken into consideration in calculating the amounts of the sources of calcium ion and magnesium ion which are necessary to arrive at the final concentrations previously discussed.

An electrolyte which aids in the preparation of colloidal suspensions may be present in the aqueous medium at the time of admixing the alkali metal silicate therewith. Examples of electrolytes include those used in preparing prior art colloidal suspensions such as the alkali metal halides, sulfates and bisulfates. Sodium chloride, sodium sulfate and sodium bisulfate are usually preferred. The electrolyte should be added in small amounts such as, for example, about 0.00001–0.1 mole per liter, but often larger or smaller amounts may be present.

The conditions under which the alkali metal silicate is admixed with the aqueous medium and reacted with the sources of calcium ion and magnesium ion are not critical provided the reaction mixture is maintained in the liquid phase. The reaction temperature may be, for example, between the freezing point and boiling point of water under the existing pressure conditions. At atmospheric pressure, the temperature is usually about 10°–90°C and often a more convenient temperature is about 20°–50°C. In many instances, ambient or normal room temperature is satisfactory.

The degree of agitation is not critical, and mild to vigorous agitation may be employed during addition of the alkali metal silicate. For the best results, the aqueous medium should be agitated sufficiently to assure rapid and uniform admixing of the alkali metal silicate. After completing the addition of the alkali metal silicate, when desired the agitation may be continued for a sufficient period of time to assure complete reaction and aging of the resulting colloidal suspension, such as for approximately 1–5 minutes to 1 hour or longer.

Upon admixing the alkali metal silicate with the aqueous medium, it takes on a turbid appearance but in most instances no significant amount of visible precipitate is formed. The colloidal suspension of the reaction product thus produced should be strongly basic and may have a pH value of, for example, approximately 10–14 and preferably about 11–13, and for best results about 12. In view of this, the initial pH value of the aqueous medium containing the dissolved sources of calcium ion and magnesium ion is of importance and should be about 6–9 and preferably about 7–8. When necessary, it is possible to adjust the pH value of the aqueous medium to the foregoing levels either before during or after addition of the alkali metal silicate by adding bases such as sodium or potassium hydroxide, or mineral acids such as sulfuric or hydrochloric acid.

The colloidal suspension may be stored for several weeks or longer while awaiting the further treatment described hereinafter. In instances where the colloidal suspension is to be stored over a substantial period of time, the pH value should be maintained at the above described level and the storage vessel is preferably a tightly capped polyethylene bottle or other inert plastic container which prevents the contents from absorbing carbon dioxide from the atmosphere.

The colloidal suspension of the reaction product is not suitable for use as a catalyst as prepared and it should be agitated sufficiently in the presence of a micelle-forming surfactant to form catalyst-containing micelles. The degree of agitation, the length of the agitation period, and the amount of the micelle-forming surfactant that is present in the colloidal suspension are controlled at levels favorable to the formation of micelles. For example, the surfactant may be present in an amount of about 0.001–0.1 mole per liter and preferably about 0.03–0.07 mole per liter for most surfactants. Smaller or larger amounts may be effective with some surfactants such as 0.0001 mole per liter or less, or 0.2 mole per liter or more. About 0.05 mole per liter often gives the best results with many surfactants.

The minimum period of agitation and the minimum degree of agitation that are required for micelle formation varies somewhat with temperature and the type and amount of surfactant. As is well understood in this art, gradually increasing these variants in the presence of an effective amount of the micelle-forming surfactant will result in micelle formation when the proper levels are reached. As a general rule, longer periods of agitation and/or more vigorous agitation are required to form micelles at lower temperatures approaching the freezing point of the colloidal suspension than at higher temperatures approaching the boiling point. In instances where the aqueous suspension has a temperature of approximately 50°–90°C., then mild agitation over a period of about 10–60 minutes is satisfactory. Often longer or shorter periods of mild to vigorous agitation may be employed such as from about 1–5 minutes to several hours at temperatures varying, respectively, between the boiling point and the freezing point. When desired, the agitation may be continued long after the catalyst-containing micelles are formed as continued agitation does not seem to have an adverse affect.

As a general rule, the micelle-forming surfactants known in the prior art may be used in practicing the present invention. Micelle-forming surfactants used in the emulsion polymerization of monomeric organic compounds are disclosed in the text *Synthetic Rubber*, by G. S. Whitby, et al., John Wiley & Sons Incorporated, New York (1954), and surface active agents in general are disclosed on pages 418–424 of the text *Organic Chemistry*, Fieser and Fieser, 2nd Edition, Reinhold Publishing Corporation, New York, N.Y. (1950), the disclosures of which are incorporated herein by reference. Examples of surfactants disclosed in the above texts include the alkali metal soaps of long chain fatty acids, and especially the sodium and potassium soaps of fatty acids containing about 14–25 carbon atoms and preferably about 16–18 carbon atoms, and the sodium and potassium soaps of the rosin acids, abietic acid and the derivatives thereof. Other micelle-forming surfactants include fats and oils such as corn oil, cotton seed oil, castor oil, soy bean oil and safflower oil which have been fully or partially saponified with alkali metal bases to produce mixtures including saponified long chain fatty acids, the mono- or di-glycerides thereof, and glycerin.

Examples of synthetic micelle-forming surfactants include the sulfonates of long chain alcohols prepared by hydrogenation of naturally ocurring fats and oils of the above types and especially sulfonated long chain alcohols containing about 10–20 and preferably about 12–14 carbon atoms, the alkali metal salts of the monosulfonates of monoglycerides such as sodium glyceryl monolaurate sulfonate, the sulfonates of succinic acid esters such as dioctyl sodium sulfosuccinate and the alkylaryl alkali metal sulfonates. Specific examples of presently preferred micelle-forming surfactants include sodium and potassium sulforicinoleate, tetrahydronaphthalene sulfonate, octahydroanthracene sulfonic acid, butyl naphthalene sulfonic acid, sodium xylene sulfonate, alkyl benzene sulfonic acid and potassium benzene sulfonate.

Sulfated long chain hydroxycarboxylic acids containing about 14–25 carbon atoms and preferably about 16–18 carbon atoms, and sulfated fats and oils containing hydroxycarboxylic acids of this type produce exceptionally good micelle-forming surfactants. At least 25% of the hydroxyl groups and preferably at least 50% should be sulfated, and up to 95–100% may be sulfated. It is usually preferred that the sulfated oils and/or long chain hydroxycarboxylic acids be neutralized with an alkali metal base, and that the corresponding alkali metal salts be added to the colloidal suspension in the form of an aqueous solution. The aqueous solution may contain at least 25% of water and preferably at least 35–40% by weight. Much larger percentages of water may be present when desired such as 75–80% or more by weight.

A very active catalyst is produced when using sulfated castor oil as the micelle-forming surfactant (Turkey Red oil.) Sulfated castor oil which has been purified sufficiently to be of U.S.P. or medicinal grade produces an exceptionally active catalyst. For the best results, the castor oil is reacted with about an equal weight of concentrated sulfuric acid(e.g., 20% by weight) at a temperature of approximately 25°–30°C. The mixture may be reacted for about 2 hours with stirring and is then neutralized with sodium hydroxide solution. The reaction mixture separates into three layers, i.e., an upper layer which is a water solution, an intermediate or oily layer, and a white curdy precipitate. The intermediate oily layer is separated from the upper and lower layers, and may be added to the colloidal suspension as the micelle-forming surfactant, in an amount, for example, of 0.001–0.1 mole per liter, and preferably about 0.005 mole per liter.

The activity of the catalyst may be increased very markedly by cooling the aqueous catalyst suspension to a temperature approaching the freezing point such as about 0–10°C., and then warming over one or more cycles. For best results, the aqueous catalyst suspension should be frozen and thawed over one or more cycles. The reason for the increased catalytic activity is not fully understood at the present time but cooling and then warming the aqueous catalyst suspension seems to increase the concentration of the catalyst-containing micelles and/or increases the catalytic activity thereof.

The aqueous suspension of the catalyst contains a relatively small percentage by weight of the active catalyst as produced. When desired, it may be concentrated by evaporating a portion of the water to produce a concentrated liquid catalyst suspension which may be stored and used more conveniently. It is also possible to prepare a dry catalyst concentrate by evaporating substantially all of the water. The preferred method of producing the dry catalyst concentrate is by flash evaporation using a technique analogous to that employed in preparing powdered milk. The catalyst concentrates produced upon partial or complete evaporation of the water content of the initially prepared aqueous suspension may be reconstituted by addition of water with little or no loss of catalytic activity. Preferably, the water is added to the dry catalyst concentrate under sufficiently vigorous conditions of agitation to assure that the catalyst micelles are resuspended and uniformly distributed.

The aqueous catalyst suspension may be used as produced in practicing the invention, but preferably it is diluted with approximately 100–10,000 parts by weight of water and then used. For better results, the catalyst suspension should be diluted with about 250–2,000 parts by weight of water before use, and for best results it should be diluted with about 500–1,000 parts by weight of water before use. The surface active agent may be added thereto when desired as previously discussed. Alternatively the dry catalyst or liquid catalyst concentrate may be admixed with water and/or the surface active agent to provide an effective catalyst concentration in the quantities previously discussed. The weight of the catalyst is calculated on a dry solids basis, i.e., the weight of the catalyst ingredients in the aqueous suspension as produced after removal of the water.

The invention is further illustrated by the following specific examples.

EXAMPLE I

This example illustrates one presently preferred process for preparing the novel catalyst used in practicing the invention.

Anhydrous calcium chloride in an amount of 0.66 gram and magnesium sulfate heptahydrate in an amount of 1.32 grams were dissolved in two liters of deionized water with stirring and warming until solution was complete. Then 95 grams of sodium silicate pentahydrate having a molecular ratio of sodium oxide to silicon dioxide of 1:1 were added to the solution with stirring and continued warming to produce a white colloidal suspension of the reaction product.

After setting for 10 minutes, the colloidal suspension was heated to 80°C. and sulfated castor oil in an amount of 50 grams was added with stirring. The average molecular weight of the sulfated castor oil was 940 and it contained 50% of water. The turbidity lessened somewhat as the colloidal suspension was heated at 80°–90°C. for 1 hour with vigorous stirring to produce catalyst micelles. The aqueous suspension of catalyst micelles thus prepared had a viscosity similar to that of water and it was used as the catalyst in certain Examples as noted hereinafter.

A dry or solid catalyst concentrate was prepared in a further run by evaporating water from the initially prepared aqueous catalyst suspension. The resulting dry catalyst concentrate was resuspended in water and there was no substantial loss of catalytic activity. In still other runs, the catalytic activity of the aqueous suspension of catalyst as initially prepared, the diluted aqueous suspension of catalyst, and the reconstituted aqueous catalyst suspension was enhanced by freezing and thawing.

EXAMPLE II

This example illustrates the preparation of additional catalyst suspensions.

Five suspensions of the catalyst were prepared from the same ingredients as used in Example I and following the general procedure of Example I. The ratios of ingredients were varied as follows:

| Ingredient | Amount of Ingredient | | | | |
|---|---|---|---|---|---|
| | Run 1 | Run 2 | Run 3 | Run 4 | Run 5 |
| Deionized water | 2 l | 1.5 l | 1.5 l | 1.5 l | 0.25 l |
| $CaCl_2$ | 0.66 g | 0.5 g | 0.5 g | 1.0 g | 0.5 g |
| $MgSO_4.7H_2O$ | 1.32 g | 1.0 g | 1.0 g | 2.0 g | 1.0 g |
| $Na_2SiO_3.5H_2O$ | 165 g | 132 g | 71 g | 185 g | 71 g |
| Sulfated Castor oil (approximately 50% by weight $H_2O$) | 100 ml | 150 ml | 150 ml | 200 ml | 150 ml |

The catalyst suspensions prepared by the above five runs were used in certain examples as noted hereinafter.

EXAMPLE III

This example illustrates the use of a catalyst suspension prepared in accordance with Example I in general veterinary practice to relieve stress and shock and to promote healing of infected and/or damaged tissue in domestic animals.

In a first series of tests, a veterinarian engaged in general practice treated a large number of dogs, cats, horses and cows with an aqueous catalyst suspension containing one volume of the catalyst suspension as prepared in accordance with Example I diluted with 1,000 volumes of water. No additional ingredients were added to the diluted aqueous catalyst suspension. The catalyst suspension was applied one to three times per day by spraying it on infected and/or damaged tissue including open sores, cuts, burns, sprains and following surgery. No further treatment was given with the exception of cleansing the infected or damaged area where necessary so as to allow the catalyst suspension to be topically applied. The rate of healing was observed closely. In instances where an amimal was initially under stress and/or shock, it was observed that both stress and shock were relieved and the animal was calmed following the application of the catalyst suspension without administering drugs. This also applied to subsequent applications of the catalyst suspension. Additionally, the infected and/or damaged tissue healed at a much more rapid rate than in a control group of animals where conventional veterinary practice was followed.

In a second series of tests, 0.001% of Gentian Violet was added to the above described diluted catalyst suspension. The results were as reported above for the first series of runs insofar as relieving stress and shock are concerned. However, the catalyst suspension containing the Gentian Violet, which is a ultra violet light absorber, was even more effective in promoting healing of open wounds than the catalyst suspension when used alone.

EXAMPLE IV

This example illustrates the use of a diluted catalyst suspension prepared in accordance with Example I and diluted with 1,000 volumes of water in the treatment of calves to promote the healing of open wounds and/or to relieve stress and shock.

In the first experiment, the catalyst suspension was used to relieve stress and shock at the time of weaning dairy calves. It is the usual custom to feed dairy calves only for the first 3 days on the mother's milk and thereafter on a milk substitute. The shock to the calf is severe when deprived of the mother's milk and prior experience has shown that approximately 20% of the calves weaned according to the conventional practice do not survive.

Over 100 dairy calves were weaned after 3 days and thereafter were given a milk substitute. Four liquid ounces of the diluted catalyst suspension were added to each 4 pints of the milk substitute over the first 24 hours following weaning. Further treatment with the catalyst suspension is not necessary unless the calf becomes sick. The catalyst suspension is effective in relieving stress and shock over a period of several days following the initial 24 hour period and apparently it is retained to some extent in the digestive tract for a sufficiently long period of time to accomplish the intended purpose. No calves were lost in this experiment due to the stress and shock accompanying weaning.

In a second experiment, beef cattle calves were weaned after 5 months. The catalyst suspension was added to their drinking water over the first day following weaning in a ratio of one-half ounce of the concentrated catalyst suspension as prepared in accordance with Example I to 20 gallons of water. The resulting drinking water contained approximately 1 volume of the catalyst suspension as prepared in accordance with Example I for each 2500 volumes of water. The 24 treatment was effective over a period of 3 weeks and no problems due from stress, shock, or disease were observed and no calves were lost. After that time, several calves contacted a disease commonly referred to as "dust pneumonia." The treatment of the drinking water with the catalyst suspension was resumed as before and the symptons of dust pneumonia were relieved without loss of calves. In each instance, stress and shock were relieved and the catalyst suspension was also effective as a therapeutic agent.

In a further experiment, calves to be branded and dehorned were separated into two groups. The first group was used as a control group, and the usual ranch practice was followed subsequent to branding and dehorning. The control group of calves had unhealed wounds resulting from the branding and dehorning for up to 6 weeks.

The second group of calves were branded and dehorned following the same practice as used on the first group with the exception of spraying the open wounds from one to three times per day with a diluted catalyst suspension prepared by diluting the catalyst suspension of Example I with 1,000 volumes of water. After each application of the diluted catalyst suspension, the treated calves were calm and stress and shock resulting from the branding and dehorning were relieved markedly. The calves also did not seem to be in pain. After a week of this treatment, the wounds resulting from the branding and dehorning were healed without loss of calves.

EXAMPLE V

This example illustrates the synergistic effect of the catalyst suspension of the invention on antibiotics when used in the treatment of cancer eye in cattle. Previous attempts to cure cancer eye with antibiotics alone were not successful. The catalyst suspension used in this Example was prepared by diluting the catalyst suspension as prepared in Example I with 1,000 volumes of water.

In the first experiment, a cow infected with cancer eye in an advanced stage was injected with 5 cc of *COMBIOTIC, admixed with 5 cc of the diluted catalyst suspension. The infected eye, which had a bulbous mass 3–6 inches in diameter thereover, was then sprayed with the diluted catalyst suspension. The cow was in a nervous agitated state prior to the treatment and was not eating. Following the treatment, the cow was released from the chute in which she was treated and immediately started eating from a food supply that was provided. The cow was clearly under much less stress than prior to the treatment. After 10 days of spraying every other day with the diluted catalyst suspension, the bulbous mass had disappeared and there was no outward sign of infection.

*Combiotic is a trademark for a mixture of biotics including penicillin and dihydrostreptomycin In a second experiment, 11 cows were obtained which were infected with cancer eye in advanced stages. The 11 cows were injected with 5 cc of COMBIOTIC admixed with 5 cc of the diluted catalyst suspension and the infected eyes were sprayed once with the diluted catalyst suspension. The cows were then fed 10 pounds per day of a commercial feed consisting of rolled oats and corn containing 20 pounds per ton of *TERRAMIX ABD-25. One quart per ton of the concentrated catalyst suspension as prepared by Example I in 10 gallons of water was sprinkled over the dry commercial feed and admixed therein. The cows were observed over a 10 day feeding period and the absence of stress and the gradual disappearance of the visible symptons of cancer eye were noted.

*Terramix ABD-25 is a commercial antibiotic sold by Charles Pfizer, Incorporated which contains vitamins A, B and D and Oxytetracycline (Terramycin), a broad spectrum antibiotic.

At the end of the test program, two cows were returned to the herd as the cure seemed to be complete to the veterinarian in charge. The other 10 cows were slaughtered under the supervision of a veterinarian who was the U.S. Department of Agriculture inspector in charge of the slaughter house. Four of the 10 cows were declared free of cancer eye and were passed for human consumption. The other six cows were rejected thereby indicating a 50% cure rate.

Prior to this experiment, there was no known effective cure for cancer eye and the 50% cure rate was considered to be remarkable. It was also believed that if the cancer eye infections had been treated at an early stage rather than at the advanced state of this experiment, the cure would have been complete in all 12 animals.

EXAMPLE VI

This example illustrates the use of a synergistic combination of antibiotics and the catalyst of the invention in treating foot rot in cattle and sheep. The catalyst suspension used in this example was prepared by diluting the catalyst suspension as prepared in accordance with Example I with 1,000 volumes of water.

In the first experiment, sheep infected with foot rot in an advanced stage were sprayed over the infected foot areas with the diluted catalyst suspension. This procedure gave relief from 1 to 2 weeks and then the infection returned. Thus, the catalyst suspension alone could not effect a permanent cure although there was temporary improvement.

In a second experiment, the sheep were injected with 2 cc of COMBIOTIC admixed with 2 cc of the diluted catalyst suspension and the infected foot areas were sprayed with the diluted catalyst suspension. This treatment resulted in a complete cure as the foot rot infection did not return.

In a further experiment, a 1700 pound Hereford bull having foot rot in an advanced stage in one foot with secondary infection in the leg and thigh thereabove was injected with a mixture of 5 cc of COMBIOTIC admixed with 5 cc of the diluted catalyst suspension. The infected foot and leg were then sprayed with the diluted catalyst suspension. By the next day, the swelling in the leg and thigh was gone and the infected foot was greatly improved. The treatment was continued for 10 days and by that time the bull was able to walk without difficulty. The cure was considered to be complete.

EXAMPLE VII

The test procedures of Examples III–VII are repeated with the exception of using the catalyst suspensions prepared by the procedure of Example II. Comparable results to those reported in Examples III–VII are obtained with the Example II catalysts.

I claim:

1. A therapeutic composition for treating warm blooded animals having damaged or infected tissue which responds to treatment with an antibiotic comprising an antibiotic therapeutically effective in treating the said damaged or infected tissue and a catalytically effective amount of a catalyst, the therapeutic composition containing the antibiotic and catalyst in amounts to administer the antibiotic in a therapeutically effective amount to treat the said damaged or infected tissue in the warm blooded animal which responds to treatment therewith and about 0.000001–1% of body weight of the catalyst, the catalyst being prepared by a process comprising admixing a water soluble alkali metal silicate with an aqueous medium containing a dissolved substance which is a source of calcium ion and a dissolved substance which is a source of magnesium ion, the aqueous medium containing said dissolved substances in amounts to provide between about $1 \times 10^{-4}$ and $1 \times 10^{-1}$ mole per liter each of calcium ion and magnesium ion, the aqueous medium containing said dissolved substances in amounts to provide a molar ratio of calcium ion to magnesium ion between about 2.0:1.0 and 1.0:2.0, the alkali metal silicate having an alkali metal oxide to silicon dioxide ratio between about 9.0:1.0 and less than 2.0:1.0 and being admixed with the aqueous medium in an amount of about 0.05–2 moles per liter, reacting the alkali metal silicate with said dissolved substances providing calcium ion and magnesium ion to produce an aqueous suspension of finely divided particles of the reaction product, admixing a micelle-forming surfactant with the aqueous medium in an amount to form catalyst micelles comprising said finely divided particles of the reaction product upon agitating the aqueous medium, and agitating the aqueous medium containing the finely divided particles of the reaction product and surfactant to form said catalyst micelles.

2. The composition of claim 1 wherein in the process for preparing the catalyst, said ratio of calcium ion to magnesium ion is between about 1.5:1.0 and 1:1:1.5.

3. The composition of claim 1 wherein in the process for preparing the catalyst, said ratio of calcium ion to magnesium ion is about 1.0:1.0.

4. The composition of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion.

5. The composition of claim 1 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion.

6. The composition of claim 1 wherein in the process for preparing the catalyst, about 0.2–0.5 mole per liter of the alkali metal silicate is admixed with the aqueous medium.

7. The composition of claim 1 wherein in the process for preparing the catalyst, the alkali metal silicate has an alkali metal oxide to silicon dioxide ratio between about 0.9:1.0 and 1.2:1.0.

8. The composition of claim 1 wherein in the process for preparing the catalyst, the alkali metal silicate is alkali metal metasilicate having an alkali metal oxide to silicon dioxide ratio of about 1.0:1.0.

9. The composition of claim 1 wherein in the process for preparing the catalyst, about 0.01–0.1 mole per liter of the surfactant is admixed with the aqueous medium.

10. The composition of claim 1 wherein in the process for preparing the catalyst, the surfactant is sulfated castor oil.

11. The composition of claim 1 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.2:0.5 mole per liter of the alkali metal silicate is admixed with the aqueous medium, and the alkali metal silicate has an alkali metal oxide to silicon dioxide ratio between about 0.9:1.0 and 1.2:1.0.

12. The composition of claim 1 wherein in the process of preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the alkali metal silicate is admixed with the aqueous medium, and the alkali metal silicate is alkali metal metasilicate having an alkali metal oxide to silicon dioxide ratio of about 1.0:1.0.

13. The composition of claim 12 wherein in the process for preparing the catalyst, the alkali metal metasilicate is sodium metasilicate having a sodium oxide to silicon dioxide ratio of about 1.0:1.0.

14. The composition of claim 12 wherein in the process for preparing the catalyst, about 0.01–0.1 mole per liter of the surfactant is admixed with the aqueous medium.

15. The composition of claim 14 wherein in the process for preparing the catalyst, the surfactant is sulfated castor oil.

16. The composition of claim 15 wherein in the process for preparing the catalyst, the alkali metal metasilicate is sodium metasilicate having a sodium oxide to silicon dioxide ratio of about 1.0:1.0.

17. The composition of claim 16 wherein in the process for preparing the catalyst, at least 50% of the hydroxy groups of the castor oil are sulfated, and about 0.03–0.07 mole per liter of the sulfated castor oil is admixed with the aqueous medium.

18. The composition of claim 12 wherein in the process for preparing the catalyst, the alkali metal silicate is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

19. The therapeutic composition of claim 1 wherein the said antibiotic is a therapeutically effective amount of a mixture of penicillin and dihydrostreptomycin.

20. A method of therapeutically treating a warm blooded animal having damaged or infected tissue which responds to treatment with an antibiotic comprising treating the warm blooded animal with a therapeutic composition containing an antibiotic in the presence of a catalyst, the said warm blooded animal having damaged or infected tissue which responds to treatment with the said antibiotic and the therapeutic composition containing a therapeutically effective amount of the antibiotic for treatment of the said damaged or infected tissue in the presence of about 0.000001–1% of the catalyst based upon the body weight of the warm blooded animal, the catalyst being prepared by a process comprising admixing a water soluble alkali metal silicate with an aqueous medium containing a dissolved substance which is a source of calcium ion and a dissolved substance which is a source of magnesium ion, the aqueous medium containing said dissolved substances in amounts to provide between about $1 \times 10^{-4}$ and $1 \times 10^{-1}$ mole per liter each of calcium ion and magnesium ion, the aqueous medium containing said dissolved substances in amounts to provide a molar ratio of calcium ion to magnesium ion between about 2.0:1.0 and 1.0:2.0, the alkali metal silicate having an alkali metal oxide to silicon dioxide ratio between about 0.9:1.0 and less than 2.0:1.0 and being admixed with the aqueous medium in an amount of about 0.05–2 moles per liter, reacting the alkali metal silicate with said dissolved substances providing calcium ion and magnesium ion to produce an aqueous suspension of finely divided particles of the reaction product, admixing a micelle-forming surfactant with the aqueous medium in an amount to form catalyst micelles comprising said finely divided particles of the reaction product upon agitating the aqueous medium, and agitating the aqueous medium containing the finely divided particles of the reaction product and surfactant to form said catalyst micelles.

21. The method of claim 20 wherein in the process for preparing the catalyst, said ratio of calcium ion to magnesium ion is between about 1.5:1.0 and 1.0:1.5.

22. The method of claim 20 wherein in the process for preparing the catalyst, said ratio of calcium ion to magnesium ion is about 1.0:1.0.

23. The method of claim 20 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion.

24. The method of claim 20 wherein in the process for preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion.

25. The method of claim 20 wherein in the process for preparing the catalyst, about 0.2–0.5 mole per liter of the alkali metal silicate is admixed with the aqueous medium.

26. The method of claim 20 wherein in the process for preparing the catalyst, the alkali metal silicate has an alkali metal oxide to silicon dioxide ratio between about 0.9:1.0 and 1.2:1.0.

27. The method of claim 20 wherein in the process for preparing the catalyst, the alkali metal silicate is alkali metal metasilicate having an alkali metal oxide to silicon dioxide ratio of about 1.0:1.0.

28. The method of claim 20 wherein in the process for preparing the catalyst, about 0.01–0.1 mole per liter of the surfactant is admixed with the aqueous medium.

29. The method of claim 20 wherein in the process for preparing the catalyst, the surfactant is sulfated castor oil.

30. The method of claim 20 wherein in the process for preparing the catalyst, the alkali metal silicate is admixed with an aqueous medium containing said dissolved substances in amounts to provide between about $1 \times 10^{-3}$ and $6 \times 10^{-3}$ mole per liter each of calcium ion and magnesium ion, the ratio of calcium ion to magnesium ion is between about 1.5:1.0 and 1.0:1.5, about 0.2:0.5 mole per liter of the alkali metal silicate is admixed with the aqueous medium, and the alkali metal silicate has an alkali metal oxide to silicon dioxide ratio between about 0.9:1.0 and 1.2:1.0.

31. The method of claim 20 wherein in the process of preparing the catalyst, the alkali metal silicate is admixed with an aqueous medium containing said dissolved substances in amounts to provide between about $2.5 \times 10^{-3}$ and $3.0 \times 10^{-3}$ mole per liter each of calcium ion and magnesium ion, the aqueous medium contains about equimolar amounts of calcium ion and magnesium ion, about 0.2–0.3 mole per liter of the alkali metal silicate is admixed with the aqueous medium, and the alkali metal silicate is alkali metal metasilicate having an alkali metal oxide to silicon dioxide ratio of about 1.0:1.0.

32. The method of claim 31 wherein in the process for preparing the catalyst, the alkali metal metasilicate is sodium metasilicate having a sodium oxide to silicon dioxide ratio of about 1.0:1.0.

33. The method of claim 31 wherein in the process for preparing the catalyst, about 0.01–0.1 mole per liter of the surfactant is admixed with the aqueous medium.

34. The method of claim 33 wherein in the process for preparing the catalyst, the surfactant is sulfated castor oil.

35. The method of claim 34 wherein in the process for preparing the catalyst, the alkali metal metasilicate is sodium metasilicate having a sodium oxide to silicon dioxide ratio of about 1.0:1.0.

36. The method of claim 35 wherein in the process for preparing the catalyst, at least 50% of the hydroxy groups of the castor oil are sulfated, and about 0.03–0.07 mole per liter of the sulfated castor oil is admixed with the aqueous medium.

37. The method of claim 31 wherein in the process for preparing the catalyst, the alkali metal silicate is admixed with an aqueous medium containing said dissolved substances in amounts to provide about $2.9 \times 10^{-3}$ mole per liter of calcium ion and about $2.7 \times 10^{-3}$ mole per liter of magnesium ion, about 0.25 mole per liter of sodium metasilicate having a sodium oxide to silicon dioxide ratio of about 1.0:1.0 is admixed with the aqueous medium, the aqueous medium contains not more than 10 parts per million by weight of carbonate ion and bicarbonate ion, the surfactant comprises sulfated castor oil and at least 50% of the hydroxy groups of the castor oil are sulfated, and about 0.05 mole per liter of the sulfated castor oil is admixed with the aqueous medium.

38. The method of claim 20 wherein the warm blooded animal is treated with a therapeutically effective amount of a mixture of penicillin and dihydrostreptomycin.

* * * * *